United States Patent [19]
Forkner et al.

[11] Patent Number: 4,750,476
[45] Date of Patent: Jun. 14, 1988

[54] ENDOSCOPE WITH MULTIPLE SECTION IMAGE TRANSMITTING ROD

[75] Inventors: John F. Forkner, South Laguna; Robert J. Freiberg, Mission Viejo, both of Calif.

[73] Assignee: Baxter Travenol Laboratories, Inc., Deerfield, Ill.

[21] Appl. No.: 909,765

[22] Filed: Sep. 19, 1986

[51] Int. Cl.$^4$ .............................................. A61B 1/06
[52] U.S. Cl. ...................................................... 128/6
[58] Field of Search ........................... 128/3, 4, 5, 6, 7

[56] References Cited

U.S. PATENT DOCUMENTS 3,257,902  6/1966  Hopkins ............................. 128/6 X
4,036,218  7/1977  Yamashita et al. ..................... 128/4
4,624,243  11/1986  Lowery et al. ......................... 128/6

*Primary Examiner*—William H. Grieb
*Attorney, Agent, or Firm*—Gordon L. Peterson

[57] ABSTRACT

An endoscope comprising a body, including an elongated tubular distal section adapted for insertion into a patient and optics for transmitting an image through the distal section so that the image can be viewed at a viewing location. The image-transmitting optics include an elongated image-transmitting rod for transmitting the image to at least a region of the distal section. The image-transmitting rod is subject to breakage by bending forces and is divided longitudinally into discrete elongated rod sections to thereby reduce the likelihood of breakage by bending forces.

11 Claims, 1 Drawing Sheet

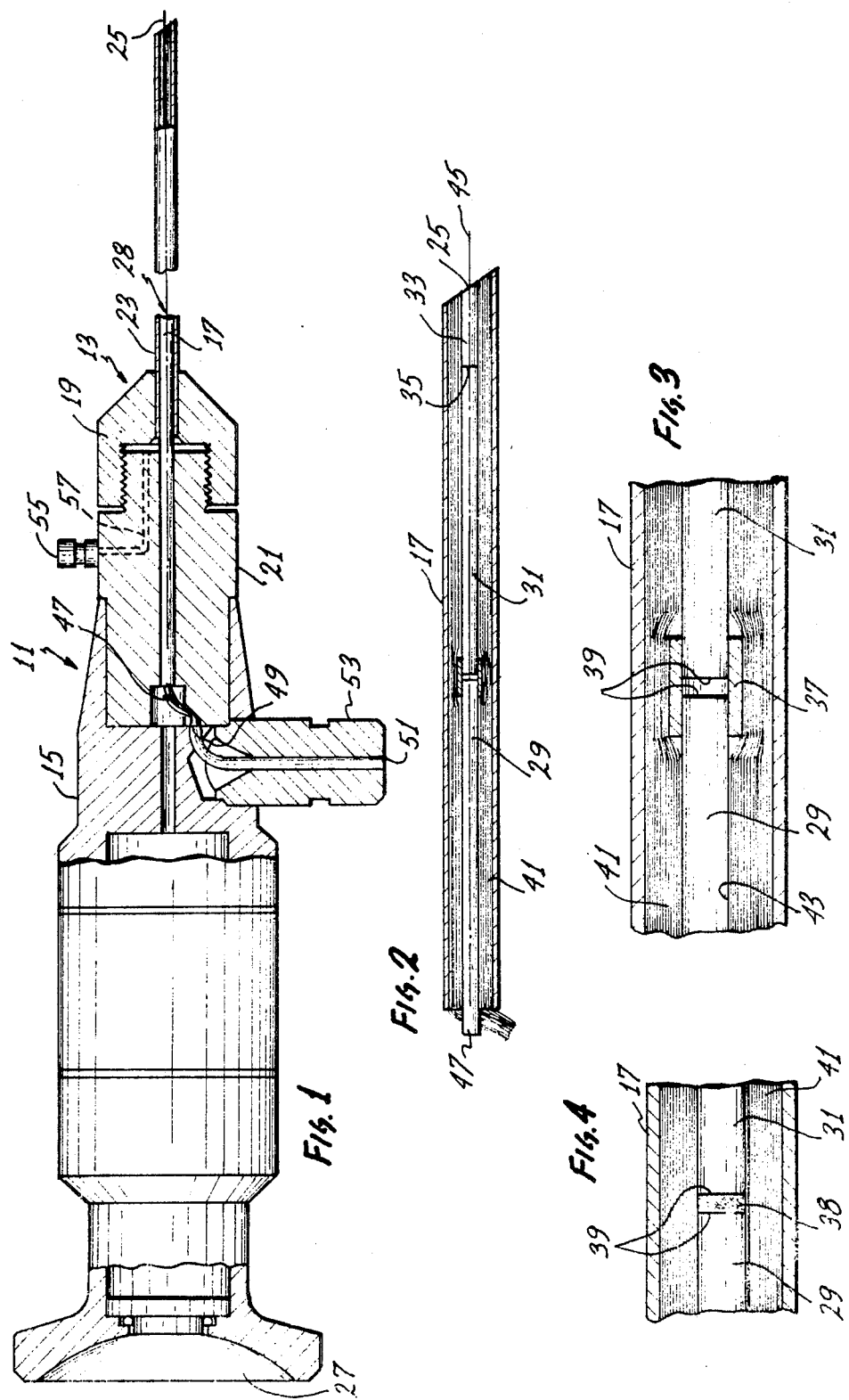

ENDOSCOPE WITH MULTIPLE SECTION IMAGE TRANSMITTING ROD

BACKGROUND OF THE INVENTION

An endoscope is used to enable a physician to view internal regions of a human or animal body. An endoscope may typically comprise a body, including an elongated tubular distal section adapted for insertion into a patient and a viewing port. Image-transmitting means is provided within the body to transmit an image through the distal section so that the image can be viewed at the viewing port. The field of view can be illuminated in various ways, such as by optical illumination fibers extending through the distal section of the endoscope.

One advantageous way to transmit the image through the distal section is with an image-transmitting rod which may, for example, be constructed of gradient index material. Image-transmitting rods, such as those constructed of gradient index material, tend to be relatively stiff and brittle and may be of very small diameter, such as 0.5 millimeter. Accordingly, image-transmitting rods of this type are subject to breakage by bending forces. An endoscope utilizing an image-transmitting rod, which may be constructed of gradient index material, is shown and described in copending application Ser. No. 909,264 filed on even date herewith entitled Distortion-Corrected Endoscope and naming John Forkner as the sole inventor. This copending application is incorporated by reference herein.

In use of the endoscope, the image-transmitting rod and the distal section of the endoscope are subjected to bending forces. These bending forces may be sufficient to break the image-transmitting rod thereby rendering the endoscope useless for its intended purpose.

SUMMARY OF THE INVENTION

This invention reduces the likelihood that the image-transmitting rod of the endoscope will be broken by bending forces. With this invention, the distal section of the endoscope can be subjected to higher bending forces without breaking the image-transmitting rod. In addition, the physician will observe a narrowing of the field of view when the distal section of the endoscope is bent excessively, and this gives the physician a chance to correct this condition before breakage occurs.

The advantageous results can be accomplished by dividing the image-transmitting rod longitudinally into discrete, elongated rod sections. The elongated sections are, therefore, shorter than the full length of the image-transmitting rod, and these shorter sections can withstand greater bending forces without breaking.

The adjacent sections of the image-transmitting rod are coupled together by a coupling which can withstand significant bending forces without breaking. For this purpose, the coupling should be somewhat pliable and flexible rather than being rigid. A rigid coupling would join the sections of the image-transmitting rod together such that the image-transmitting rod would be more likely to break than if the coupling were somewhat pliable. Various flexible couplings, including a rubber-like flexible adhesive can be used. A preferred coupling includes a sleeve receiving end portions of the adjacent sections of the image-transmitting rod for coupling such adjacent sections together. The sleeve should be pliable or flexible and can advantageously include shrink tubing of plastic material.

The distal section of the endoscope typically includes an elongated, resiliently bendable tube, and the image-transmitting rod extends within the tube. To enable the physician to see the body region to be observed, it is necessary to transmit light to the distal end of the endoscope, and this can be accomplished with light-transmitting fibers which extend within the tube to a location adjacent the distal end of the tube. To protect and cushion the image-transmitting rod, the fibers preferably form a tunnel, and the image-transmitting rod extends at least partially through the tunnel. As a group, the image-transmitting fibers are somewhat soft and do not transmit all of the bending forces applied to the tube to the image-transmitting rod.

This invention is applicable to image-transmitting rods of gradient index material or of any other material which has a tendency to break as a result of bending forces during use of the endoscope. When gradient index material is used, the image-transmitting rod is preferably divided longitudinally at a region where light conducted by the image-transmitting rod is substantially collimated. This reduces the sensitivity to alignment errors of the rod sections and reduces the visibility of any minute particles at the interface of the rod sections. To obtain a division where the light is substantially collimated, the division should occur at N/4 pitches where N is an odd integer.

The number of elongated sections can be selected to provide the desired resistance to breakage from bending forces. If one length division is to occur, it preferably occurs near the midpoint of the image-transmitting rod. The pitch length for the rod sections need not be the same. However, if the pitch lengths are different, magnification of the image will result.

The invention, together with additional features and advantages thereof, may best be understood by reference to the following description taken in connection with the accompanying illustrative drawing.

BRIEF DESCRIPTION OF THE DRAWING

FIG. 1 is an elevational view partially in section of one form of endoscope constructed in accordance with the teachings of this invention.

FIG. 2 is an enlarged, sectional view illustrating a portion of the distal section of the endoscope.

FIG. 3 is an enlarged, fragmentary sectional view illustrating the region of the distal section where adjacent elongated rod sections are coupled together.

FIG. 4 is a view similar to FIG. 3 but showing an alternative embodiment of the invention.

DESCRIPTION OF THE PREFERRED EMBODIMENT

FIG. 1 shows an endoscope 11 which generally comprises a tubular, disposable distal section 13 and a reusable eyepiece housing 15. The distal section 13 includes a tube 17 of a suitable metal, such as stainless steel, a nut 19, a connector 21 and an irrigation cannula 23.

Image-transmitting means transmits an image from a distal end 25 of the distal section 13 so that an image can be viewed at a viewing location 27. The image-transmitting means includes an elongated image-transmitting rod 28 extending through the tube 17 and divided longitudinally into discrete, elongated rod sections 29 and 31 (FIG. 2) which form a portion of the disposable distal section. The image-transmitting means also includes an objective lens 33 adhered to the distal end of the rod section 31 at an interface 35.

In the illustrated embodiment, the rod sections 29 and 31 and the objective lens 33 are constructed of gradient index material. The objective lens 33 is slightly less than ¼ pitch in length and forms an image at the interface 35. For example, the rod section 31 may have a pitch length of 2.25 pitches, and the rod section 29 may have a pitch length of 2 pitches. With this construction, the light leaving the rod section 31 and entering the rod section 29 is substantially collimated. In this embodiment, the diameters of the rod sections 29 and 31 and of the objective lens 33 are 0.5 millimeter.

The rod sections 29 and 31 have confronting end portions which are received within a sleeve 37 of plastic shrink tubing. The rod sections 29 and 31 have confronting faces 39, which may be slightly spaced apart or may be contiguous. In any event, the sleeve 37 tightly retains the confronting end portions of the rod sections 29 and 31. The sleeve 37 is pliable or flexible so that the joint formed thereby is somewhat bendable.

In an alternative embodiment of the invention, sleeve 37 may be replaced by a rubber-like, flexible adhesive filling 38 interposed between the ends 39 of the rod sections 29 and 31 (FIG. 4).

Light-transmitting fibers 41 extend within the tube 17 to the distal end 25 and form a tunnel 43 (FIG. 3) into which the rod sections 29 and 31 extend. The light-transmitting fibers 41 cushion the rod sections 29 and 31 against bending loads from the tube 17.

The distal end 25 of the distal section 13 may be cut at an angle relative to the optical axis 45 to provide an offset field of view as described in the above-mentioned copending application. This introduces distortion as described in the copending application which can be corrected by distortion-correcting optics (not shown) carried within the eyepiece housing 15 as described in the copending application. The features of this invention relating to the rod sections 29 and 31 can be used with or without the offset field of view and the distortion-correcting optics.

In this embodiment, the rod section 29 extends proximally to a proximal end 47 which lies proximally of the tube 17. The illumination fibers 41 extend proximally to a location 49 at the proximal end of the connector 21. Illumination can be provided to the location 49 by optical fibers 51 which extend through an optical fiber connector member 53 and terminate in confronting relationship with the proximal ends of the illumination fibers 41 at the location 49. Irrigation fluid can be provided to the distal end 25 from a fitting 55 through a passage 57 and an annular space between the irrigation cannula 23 and the tube 17 in a conventional manner.

The endoscope 11 can be used in a conventional manner by inserting the distal section 13, and in particular, the tube 17, into the appropriate body region with the illumination fibers 41 conducting illumination to the distal end 25 to illuminate the field. The surgeon can view the body region at the viewing location 27 of the eyepiece housing 15. During use, the tube 17 is subjected to bending loads, and the tube resiliently bends under these loads. Some of these bending loads are transmitted to the rod sections 29 and 31. However, because the rod sections are separate, discrete members, they are more able to withstand the bending loads without breaking. The sleeve 37 flexes to help accommodate the bending loads, and the illumination fibers 14 do not transmit all of the bending loads from the tube 17 through the rod sections 29 and 31. Consequently, the image-transmitting rod 28 through the tube 17 is provided with significant protection against breakage due to bending loads.

Although an exemplary embodiment of the invention has been shown and described, many changes, modifications and substitutions may be made by one having skill in the art without necessarily departing from the spirit and scope of this invention.

We claim:

1. An endoscope comprising:
a body including an elongated tubular distal section adapted for insertion into a patient and a proximal viewing location;
image-transmitting means for transmitting an image through the distal section so that the image can be viewed at the viewing location, said image-transmitting means having an optical axis;
said image-transmitting means including an elongated image-transmitting rod of gradient index material for transmitting the image through at least a region of the distal section and a lens positioned distally of the image-transmitting rod; and
said image-transmitting rod being subject to breakage by bending forces and being divided longitudinally into discrete elongated rod sections to thereby reduce the likelihood of breakage by bending forces.

2. An endoscope as defined in claim 1 including a sleeve within said body receiving end portions of adjacent rod sections of the image-transmitting rod for coupling such adjacent rod sections together.

3. An endoscope as defined in claim 2 wherein said sleeve includes shrink tubing.

4. An endoscope as defined in claim 1 including flexible coupling means for coupling together adjacent rod sections.

5. An endoscope as defined in claim 1 wherein said distal section includes an elongated resiliently bendable tube and said image-transmitting rod extends within said tube.

6. An endoscope as defined in claim 5 including light-transmitting fibers extending within the tube to a location adjacent a distal end of the tube and forming a tunnel, said image-transmitting rod being at least partially in the tunnel and being cushioned by the light-transmitting fibers.

7. An endoscope as defined in claim 1 wherein end portions of adjacent rod sections of said image-transmitting rod are fastened together using transparent flexible adhesive, there being a finite gap between the ends of said rod sections.

8. An endoscope comprising:
a body including an elongated tubular distal section adapted for insertion into a patient and a proximal viewing location;
image-transmitting means for transmitting an image through the distal section so that the image can be viewed at the viewing location, said image-transmitting means having an optical axis;
said image-transmitting means including an elongated image-transmitting rod of gradient index material for transmitting the image through at least a region of the distal section;
said image-transmitting rod being subject to breakage by bending forces and being divided longitudinally into discrete elongated rod sections to thereby reduce the likelihood of breakage by bending forces; and said image-transmitting rod being divided longitudinally at a region where light conducted by the image-transmitting rod is substantially collimated.

9. An endoscope as defined in claim 8 including a flexible sleeve receiving portions of adjacent rod sections of the image-transmitting rod for coupling such adjacent rod sections together.

10. An endoscope as defined in claim 9 wherein said distal section includes an elongated resiliently bendable tube and said image-transmitting rod extends within said tube, said endoscope includes light-transmitting fibers extending within the tube to a location adjacent a distal end of the tube and forming a tunnel, and said image-transmitting rod being at least partially in the tunnel and being cushioned by the light-transmitting fibers.

11. An endoscope as defined in claim 8 wherein end portions of adjacent rod sections of said image-transmitting rod are fastened together using transparent flexible adhesive, there being a finite gap between the ends of said rod sections.

* * * * *